United States Patent [19]

Okuzumi et al.

[11] 4,157,437
[45] Jun. 5, 1979

[54] ADDITION COPOLYMERS OF LACTIDE AND GLYCOLIDE AND METHOD OF PREPARATION

[75] Inventors: Yuzi Okuzumi, Belle Mead; A. Darline Mellon, Bridgewater; David Wasserman, Springfield, all of N.J.

[73] Assignee: Ethicon, Inc., Somerville, N.J.

[21] Appl. No.: 914,692

[22] Filed: Jun. 12, 1978

Related U.S. Application Data

[62] Division of Ser. No. 809,737, Jun. 24, 1977.

[51] Int. Cl.$^2$ ............................................. C08G 63/08
[52] U.S. Cl. .................................... 528/354; 260/823
[58] Field of Search ......................... 528/354; 260/823

[56] References Cited

U.S. PATENT DOCUMENTS

| | | | |
|---|---|---|---|
| 3,297,033 | 1/1967 | Schmitt et al. ..................... | 128/335.5 |
| 3,422,181 | 1/1969 | Chirgwin ............................. | 264/345 |
| 3,442,871 | 5/1969 | Schmitt et al. ..................... | 260/78.3 |
| 3,636,956 | 1/1972 | Schneider .......................... | 128/335.5 |
| 3,839,297 | 10/1974 | Wasserman et al. ................ | 260/78.3 |
| 3,867,190 | 2/1975 | Schmitt et al. ..................... | 427/2 |

*Primary Examiner*—Earl A. Nielsen
*Attorney, Agent, or Firm*—Wayne R. Eberhardt

[57] ABSTRACT

Relatively high molecular weight, fiber-forming, crystalline copolymers of lactide and glycolide are prepared in a two-stage polymerization process. In the first stage there is prepared a random copolymer of a major proportion of an optically active lactide with a minor proportion of glycolide or d,l-lactide. In the second stage, a major amount of glycolide and a minor amount of lactide monomers are admixed with the copolymer of the first stage and the polymerization resumed until there is obtained a high molecular weight addition copolymer of lactide and glycolide containing from about 50 to 75 wt percent of units derived from glycolide. The polymer is fiber-forming and useful in the preparation of absorbable surgical sutures.

13 Claims, No Drawings

ADDITION COPOLYMERS OF LACTIDE AND GLYCOLIDE AND METHOD OF PREPARATION

This is a division of application Ser. No. 809,737, filed June 24, 1977.

BACKGROUND OF THE INVENTION

1. Field of the Invention

This invention relates to synthetic absorbable sutures, and more particularly, to sutures prepared from a novel polymer derived from lactide and glycolide.

2. Description of the Prior Art

Homopolymers and copolymers of lactide and glycolide are well-known in the preparation of synthetic absorbable sutures as disclosed, for example, in U.S. Pat. Nos. 3,636,956, 2,703,316, 3,468,853, and 3,565,869. Preferred polymers are polyglycolide or copolymers of glycolide with L(−)-lactide which are highly crystalline, fiber-forming materials that can be extruded into fibers and have good physical properties and reasonable absorption times when implanted in living animal tissue.

Copolymers of lactide and glycolide for use in the preparation of surgical sutures are presently limited to a narrow range of compositions, namely, those copolymers which contain about 80 percent by weight glycolide. Random copolymers containing less than about 80 percent glycolide to about 40 percent glycolide are found to be of low crystallinity, and sutures prepared from such polymers are characterized by low tensile strength and poor strength retention in living animal tissue. Polymers containing less than about 40 percent by weight glycolide and up to 100 percent lactide are fiber-forming and result in strong suture materials, but tensile strength retention and/or the rate of absorption of such sutures in living animal tissue is typically less than desired.

It is an object of the present invention to provide copolymers of lactide and glycolide having less than about 75 percent by weight glycolide which are nevertheless highly crystalline, fiber-forming materials. It is another object of this invention to provide absorbable sutures comprised of a copolymer of lactide and glycolide containing less than about 75 percent glycolide. It is a further object of this invention to provide a method for preparing highly crystalline polymers of lactide and glycolide containing from about 50 percent to 75 percent by weight glycolide.

SUMMARY

In accordance with the present invention, highly crystalline, fiber-forming addition copolymers of lactide and glycolide having from 50 percent to 75 percent by weight glycolide are obtained by first preparing a copolymer containing at least about 60 percent lactide, and thereafter admixing that polymer with additional lactide and glycolide monomers and resuming the polymerization to obtain the final polymer product. The ratio of lactide to glycolide monomers in the second stage of the polymerization is selected to provide a final polymer product having the desired composition of from about 50 percent to 75 percent by weight glycolide.

By the method of the present invention there are obtained lactide-glycolide addition copolymers which are highly crystalline and useful in forming fibers for surgical sutures. Sutures prepared from such polymers have significantly higher initial tensile strength and better tensile strength retention in living animal tissue than sutures prepared from random copolymers of similar molar composition.

DESCRIPTION OF PREFERRED EMBODIMENTS

In the following description and examples, all parts and percentages are by weight unless otherwise specified.

The method of the present invention comprises a two-stage polymerization process. In the first stage there is a random copolymerization of an optically active lactide and glycolide monomers with the lactide component comprising at least about 60% of the monomer mixture. The polymerization is carried out in a conventional manner using a polymerization reactor equipped with heating and stirring means and in the presence of a polymerization catalyst such as stannous octoate. The polymerization is conducted with pure and dry reactants and under an atmosphere of dry nitrogen at temperature sufficient to maintain the reaction mixture in a molten state until the polymerization is complete. Random polymerization of lactideglycolide copolymers is described in U.S. Pat. Nos. 3,639,956 and 3,792,010, particularly Example XVII and VIII thereof respectively, and the specification of these patents are incorporated herein by reference for their teaching in this regard.

The second stage of the polymerization method of the present invention consists of further polymerizing the polymer of the first stage with additional lactide and glycolide monomer. In one embodiment, the polymer product of the first stage is solidified by cooling, then ground and dried under vacuum. The ground polymer is intimately admixed with additional amounts of dry glycolide and optically active lactide monomer, the respective quantities of these monomers being selected to provide a final polymer having from 50 to 75 percent glycolide.

The polymer-monomer mixture is charged into a polymerization reactor equipped with heating and stirring means, and the polymerization carried out under a dry nitrogen atmosphere using a procedure which is basically identical to that followed in the first stage. The temperature of the reactor is controlled to maintain the reactants in a molten state. Following completion of the polymerization reaction, the polymer product is discharged, solidified by cooling, ground into a powder, and dried under vacuum.

As a permissible alternative polymer composition, the first stage polymerization may be of optically active L(−)-lactide or D(+)-lactide with optically inactive d,l-lactide to form a lactide copolymer. For purposes of clarity, the ensuing description and example refer primarily to the polymerization of L(−)-lactide and glycolide in the first stage, but it is understood that D(+)-lactide may be used in place of L(−)-lactide, and d,l-lactide may be used in place of glycolide.

As an alternative method, the second stage of the polymerization process of the present invention may follow directly upon completion of the first stage by adding the required lactide and glycolide monomers directly to the molten polymer obtained in the first stage. The final polymer product is thereby obtained by a semicontinuous process without the necessity for cooling and grinding the random copolymer product of the first stage. It is important, however, that the monomers be added together as a mixture and that the stirring means in the reactor be capable of quickly and efficiently distributing the added monomers uniformly throughout the molten polymer.

While not wishing to be bound by theory, it is believed that the method of the present invention results in the lactide and glycolide monomers of the second stage grafting onto reactive end groups of the high lactide polymer of the first stage, to form a highly crystalline ordered copolymer having sequential units of high lactide and high glycolide polymers. It is believed that the final product also contains small amounts of other copolymers of various compositions and structures in solution with the ordered copolymer. For the sake of convenience, the polymer products of the present invention are sometimes referred to herein as "addition copolymers", it being understood that this term includes the sequential ordered copolymers as well as mixtures of such ordered copolymers with minor amounts of other copolymers of lactide and glycolide.

The polymers of the present invention are generally extractable with chloroform only to the extent of less than about 5 percent by weight. The polymers are thereby distinguished from simple mixtures of high lactide and high glycolide random copolymers having the same relative lactide-glycolide composition since in such mixtures, the entire high lactide component is extractable. The low level of extractables in the polymers of the present invention suggest that only a minor proportion of the high lactide copolymer from the first stage of the reaction survives the second stage without further polymerization.

The high lactide random copolymer of the first stage reaction may contain from 60 percent to 90 percent optically active lactide, and from 10 percent to 40 percent glycolide or d,1-lactide. A particularly preferred composition is one containing from 65 percent to 75 percent lactide and 25 percent to 35 percent glycolide.

The monomer mixture reacted in the second stage of the polymerization may contain from about 70 percent to 90 percent glycolide and 30 percent to 10 percent lactide. A particularly preferred composition is one containing from 80 percent to 90 percent glycolide.

The final copolymer product of the present invention may contain from about 50 percent to 75 percent glycolide and 50 percent to 25 percent lactide. A particularly preferred composition is one containing from 55 percent to 65 percent glycolide. The final copolymer is characterized by having an inherent viscosity of at least 1.20 as determined on a 0.1 percent solution of the polymer in hexafluoroisopropanol or chloroform at 25° C., a melting point of at least about 160° C., and a crystallinity of at least about 15 percent.

It is essential to the method of the present invention that the high lactide copolymer be prepared in the first stage, and the high glycolide monomer mixture be introduced in the second stage. If the reverse is attempted, the result is a low molecular weight, largely amorphous copolymer or mixture of copolymers which is unsuitable for formation of strong, orientable fibers. In a like manner, random copolymers of lactide and glycolide containing from about 50 percent to 75 percent glycolide are noncrystalline compositions and generally not desirable for the manufacture of surgical sutures.

The polymers of the present invention are melt extruded and drawn in accordance with conventional procedures to form filaments useful as surgical sutures. Such filaments are characterized by having a straight tensile strength and knot strength of at least about 40,000 psi and 30,000 psi respectively, straight tensile strength retention in vivo of at least about 40 percent after 14 days, and substantially complete absorption in vivo within about 120 days. The filaments are further characterized by a crystallinity of at least about 15 percent, and an inherent viscosity of at least about 1.0 as determined on a 0.1 percent solution in HFIP or $CHCl_3$ at 25° C.

The method and product of the present invention is further illustrated by the following examples.

EXAMPLE 1

70/30 Random Copolymer of L(−)-Lactide and Glycolide

There is charged into a metal reactor provided with an agitator and a heating jacket 4180 g of pure dry L(−)-lactide (recrystallized from toluene), 1813 g of pure dry glycolide (distilled and twice recrystallized from ethyl acetate), 12.2 ml of a 0.33 molar solution of stannous octoate in toluene, and 4.23 ml of a dioxane solution containing 0.1 g distilled diethylene glycol per ml.

The solvents are vaporized off and the charge is placed under an atmosphere of dry nitrogen. The temperature of the reactor is increased to 180° C. and maintained for 30 minutes. The resulting copolymer is discharged as a viscous melt, cooled and ground to a fine powder. The ground copolymer is dried under vacuum at 0.1 mm and at room temperature for 24 hours, and maintained at 50° C. for an additional 24 hours. The copolymer is then cooled to ambient temperature and stored at 0.1 mm until used. The polymerization conversion is determined to be 97.8 percent.

The polymerization product is a clear amber, relatively tough copolymer which is amorphous by X-ray determination. Inherent viscosity as determined on a 0.1 percent solution in chloroform at 25° C. is 1.66 dl/g.

EXAMPLE 2

35/65 Addition Copolymer of L(−)-Lactide and Glycolide

Into a polymerization reactor is charged 59.5 g of the copolymer of Example 1, 10.9 g of pure L(−)-lactide, and 79.2 g of pure glycolide. The reaction mixture is placed under an atmosphere of dry nitrogen and heated with stirring to temperature about 200° C., and maintained at this temperature for 30 minutes.

The resultant polymer is cooled, ground and dried at room temperature under 0.1 mm vacuum for 16 hours, and maintained at 70° C. for an additional 7 hours. The resulting light tan, tough, opaque copolymer has a crystalline melting point of 195°–200° C. as determined by differential scanning calorimetry. Inherent viscosity as determined at 25° C. for a 0.1 percent solution in hexafluoroisopropanol is 1.47 dl/g. The polymer exhibits 30 percent crystallinity as determined by X-ray diffraction.

Twenty-five grams of the polymer is charged into the barrel of a Model 3211 Instron Rheometer fitted with a 40 mil die having an L/D of 24:1. The barrel had been preheated to a temperature of 210° C. The polymer is extruded at the rate of 88 cubic centimeters per hour. The resulting filament is collected on a spool at a speed which results in a diameter of about 20 mils. The filament is drawn six times at 60° C. to obtain a monofilament with a diameter of 9 mils having 64,000 psi straight tensile strength at break and 40,000 psi knot strength at break.

EXAMPLE 3

31/69 Addition Copolymer of L(—)-Lactide and Glycolide

Into a polymerization reactor is charged 35.6 g of pure dry L(—)-lactide, 15.4 g of pure dry glycolide, 0.11 ml of a 0.33 molar solution of stannous octoate in toluene and 0.036 g of pure crystalline glycolic acid. The reaction mixture is placed under an atmosphere of nitrogen and heated with stirring to a temperature of 180° C. for 30 minutes and 200° C. for an additional 30 minutes.

To the clear, molten, viscous copolymer is added a mixture of 12.8 g of pure dry L(—)-lactide and 93 g of pure dry glycolide. The reaction mixture is again placed under an atmosphere of dry nitrogen and the temperature is increased to 210° C. Stirring is continued for approximately one hour.

The resulting polymer is discharged, cooled, ground and dried under 0.1 mm vacuum at room temperature for 24 hours. The resulting light tan, translucent, tough copolymer has an inherent viscosity as determined at 25° C. in hexafluoroisopropanol of 1.22 dl/g. The melting point is 194°–202° C. as determined by Mettler hot stage microscopy and the polymer is birefringent and composed of small spherulites.

Twenty-five grams of copolymer is charged into the barrel of a Model 3211 Instron Rheometer fitted with a 30 mil die. Polymer is extruded at 88 cc per hour at 204° C. The properties of the resulting monofilament are stated in Table I.

EXAMPLE 4

90/10 Random Copolymer of L(—)-Lactide and DL-Lactide

Into a polymerization reactor is charged 129.6 g of pure dry L(—)-lactide, 14.4 g of pure dry d,1-lactide, 0.6 ml of a 0.33 molar solution of stannous octoate in toluene, and 1.06 ml of dioxane solution containing 0.1 g/ml of glycolic acid. The solvents are removed by vaporization and the charge is placed under an atmosphere of dry nitrogen. The charge is heated with stirring for 20 minutes at 180° C., 20 minutes at 190° C. and 20 minutes at 210° C. The resultant polymer is discharged, cooled, ground and dried. Inherent viscosity as determined in chloroform at 25° C. is 1.80.

EXAMPLE 5

34/66 Addition Copolymer of Lactide and Glycolide

Into a polymerization reactor is charged 34.4 g of the polymer prepared in Example 4, 12.4 g of pure dry L(—)-lactide, 89.8 g of pure dry glycolide and 0.91 ml of a dioxane solution containing 0.1 g/ml of glycolic acid. The charge is placed under an atmosphere of nitrogen and heated with stirring to 180° C. for 30 minutes and 200° C. for an additional 30 minutes. The resulting polymer was discharged, cooled, ground and dried under vacuum at 0.1 mm and room temperature for 16 hours. The ground polymer is maintained under vacuum for an additional 6 hours at 80° C. and then cooled to ambient temperature. The inherent viscosity of the polymer determined at 25° C. on a 0.1 percent solution in hexafluoroisopropanol is 1.78. The polymer has a melting point of 196° C. as determined by differential scanning calorimetry and a crystallinity of 21 percent as determined by X-ray diffraction.

Twenty-five grams of copolymer is charged into the barrel of a rheometer as in Example 3. The barrel is fitted with a 40 mil die and is preheated to 220° C. and the polymer is extruded at 88 cc per hour. The properties of the resulting monofilament are given in Table I.

TABLE I

|  | Example 3 | Example 5 |
|---|---|---|
| Extrusion temperature | 204° C. | 220° C. |
| Draw ratio | 6x | 6x |
| Draw temperature | 56° C. | 66° C. |
| Diameter | 8.0 mils | 8.9 mils |
| Straight tensile strength | 65.000 psi | 71,000 psi |
| Knot tensile strength | 49,000 psi | 64,000 psi |
| Elongation | 58% | 42% |

EXAMPLE 6

In Vivo Properties of Lactide/Glycolide Monofilaments

Oriented monofilaments of lactide/glycolide addition copolymers of various compositions prepared in accordance with the previous examples are cut into 25–30 inch lengths and sterilized with ethylene oxide. Short lengths of the sterile fibers are implanted subcutaneously in rats to determine breaking strength retention, and implanted intramuscularly to determine the rate of absorption in accordance with conventional techniques for in vivo evaluation of absorbable sutures. The implanted fibers were recovered and evaluated after 7, 14 and 21 days. The compositions of the test fibers and the resultant data are given in Tables II and III. Comparative data is also provided for a comparable lactide/glycolide random copolymer control fiber to illustrate the poor strength retention of such copolymers when utilized as surgical sutures. It is noted that tissue reaction is minimal in all cases.

TABLE II

% Breaking Strength Retention of Sterile Monofilaments of Lactide/Glycolide Copolymers Implanted in Rats

| Final lactide/glycolide w/w ratio | Days postimplantation | | |
|---|---|---|---|
|  | 7 | 14 | 21 |
| 25/75 Random | 30 | 0 | 0 |
| 35/65 Addition | 85 | 61 | 33 |
| 40/60 Addition | 82 | 57 | 14 |
| 50/50 Addition | 86 | 68 | 56 |

TABLE III

Absorption of Sterile Monofilaments of Lactide/Glycolide Copolymers Implanted in Rats

| Final lactide/glycolide w/w ratio | % Suture area remaining | |
|---|---|---|
|  | 60 days | 90 days |
| 35/65 Addition | 3 | 0 |
| 40/60 Addition | 55 | Traces |
| 50/50 Addition | 62 | 14 |

EXAMPLE 7

40/60 Addition Copolymer of L(—)-Lactide/Glycolide

Into a polymerization reactor having a nitrogen atmosphere is charged 2,332 g of L(—)-lactide, 805 g of glycolide, 19.1 ml of a 0.33 molar solution of stannous octoate in toluene, and 2.197 g of glycolic acid, all reactants being pure and dry. The reaction mixture was slowly heated with stirring to 200° C. and maintained at 200° C. for 45 minutes. To the molten reaction mixture was then added with stirring, a mixture of monomers consisting of 468 g L(−)-lactide and 3,395 g glycolide. The temperature of the reaction mixture was slowly increased to 217° C. and maintained at this temperature for 45 minutes to complete the polymerization reaction.

The polymerization product was discharged from the reactor, solidified, ground and dried under vacuum for 24 hours. The ground polymer was maintained at 90° C. under vacuum for 24 hours. The resulting copolymer had an inherent viscosity of 1.27 in hexafluoroisopropanol at 25° C.

The copolymer was converted to a multifilament yarn utilizing a one inch diameter, vertical screw extruder equipped with a metering pump and a 10 hole 20 mil diameter spinneret. The extruder temperature profile was established to obtain a polymer melt temperature of 440° F. at a point above the spinneret. The polymer was melt spun into air and collected at a constant take-up speed at about 524 grams per hour. The yarn was drawn five times its original length over hot rolls maintained at 145° F. An oriented yarn of 60 denier having a tenacity of 4.3 g per denier with 38 percent elongation was obtained.

The oriented yarn was braided with a 16×3 end construction to yield a braid of 14.8 mil diameter having a straight tensile strength of 43,500 psi, knot break strength of 34,787 psi, and 30 percent elongation. In vivo strength retention determined in accordance with the procedure of Example 6 was determined to be as follows:

|  | Days in vivo | | |
|---|---|---|---|
|  | 7 | 14 | 21 |
| % Original strength retained | 60 | 41 | 17 |

EXAMPLE 8
40/60 Addition Copolymer of L(−)-Lactide/Glycolide

Into a polymerization reactor having a nitrogen atmosphere is charged 2,000 g of L(−)-lactide, 690 g of glycolide, 5.5 ml of 0.33 molar stannous octoate in toluene, and 1.885 g of glycolic acid, all reactants being pure and dry. The reaction mixture was gradually heated with stirring to 200° C. and maintained at that temperature for 45 minutes to complete the first phase of the polymerization reaction.

To the clear, molten, viscous copolymer is added a mixture of monomers consisting of 401 g of L(−)-lactide and 2,910 g of glycolide. The reaction mixture is heated to 217° C. with stirring and maintained at that temperature for 45 minutes to complete the reaction.

The product was discharged from the reactor, solidified, ground and dried under vacuum for 24 hours. The ground polymer was maintained at 90° C. under vacuum for an additional 24 hours. The resulting copolymer had an inherent viscosity of 1.40 in hexafluoroisopropanol at 25° C.

The copolymer was converted to a multifilament yarn utilizing a one-inch diameter, vertical screw extruder equipped with a metering pump and a 10 hole 20 mil spinneret. The extruder temperature profile was established to obtain a polymer melt temperature of 250° C. at a point above the spinneret. The polymer was melt spun into air and collected at a constant take-up speed at about 500 g per hour. The filaments were drawn four times their original length over hot rolls maintained at 145° F. An oriented yarn of 76 denier having a tenacity of 4.4 g per denier with 34 percent elongation and a crystallinity of 16 percent was obtained.

The oriented yarn was braided with eight carriers to obtain a braid of 11 mil diameter having a straight tensile strength of 51,400 psi, knot break strength of 37,800 psi, and 24 percent elongation. The braid was annealed at 80° C. for 6 hours under a nitrogen atmosphere, cut into 3 ft long sutures, sterilized by ethylene oxide and implanted in rats to determine in vivo tensile strength retention and absorption rate with the following results:

| Tensile Strength Retention | | | | |
|---|---|---|---|---|
|  | Days in vivo | | | |
|  | 0 | 7 | 14 | 21 |
| Break strength remaining (%) | 100 | 81 | 54 | 31 |
| Absorption | | | | |
|  | Weeks in vivo | | | |
|  | 4 | 6 | 8 | 10 |
| Suture area remaining (%) | 100 | 93 | 12 | 0 |

Examples 9-15 presented in Tables IV(a) and IV(b) are further lactide/glycolide addition copolymers prepared in accordance with the method of the present invention. Data on polymer composition and properties are set forth in the tables together with comparable data for a random copolymer and the product of Example 2. It is interesting to note that the polymers prepared in accordance with the present invention have higher inherent viscosities and well defined melting points as compared to the random copolymer of similar molar composition.

Polymer hydrolysis rates were obtained by determining the weight loss of polymer chips immersed in a phosphate buffer solution for the time and at the temperature indicated. The phosphate buffer solution is comprised of a solution of 27.6 g sodium dihydrogenphosphate monohydrate in 1,000 ml of water adjusted to a pH of 7.25 with sodium hydroxide.

Polymers were melt extruded and drawn as hereinbefore described to obtain monofilaments which were evaluated for initial breaking strength and breaking strength retention in vivo. The data as presented in Table IV(b) again illustrates the improved properties of filaments prepared from the addition copolymers of the present invention as compared with a random copolymer of comparable composition.

TABLE IV (a)

| Example | Wt ratio of lactide/glycolide | | | Monofilament properties | | | | |
|---|---|---|---|---|---|---|---|---|
| | Initial polymer | Addition monomer | Addition polymer | Tensile strength | | Tensile strength remaining | | |
| | | + → | | Straight psi 10₃ | Knot psi 10₃ | 7 days % | 14 days % | 21 days % |
| Control | 40/60 | 0 | 40/60 | 53 | 36 | — | 0 | 0 |
| 2 | 70/30 | 12/88 | 35/65 | 64 | 45 | 78 | 67 | 31 |
| 9 | 70/30 | 12/88 | 40/60 | 67 | 41 | 82 | 57 | 14 |
| 10 | 70/30 | 12/88 | 45/55 | 72 | 35 | 70 | 48 | — |
| 11 | 87/13 | 12/88 | 35/65 | 60 | 37 | 85 | 61 | 33 |
| 12 | 87/13 | 12/88 | 50/50 | 58 | 38 | 86 | 68 | 56 |
| 13 | 78/22 | 12/88 | 35/65 | 71 | 50 | 95 | 45 | 0 |
| 14 | 78/22 | 12/88 | 45/55 | 63 | 45 | 86 | 65 | 30 |
| 15 | 78/22 | 18/72 | 50/50 | 58 | 31 | 75 | 62 | 16 |

TABLE IV (b)

| Example | Inherent Viscosity* | Melting point °C. | Wt % of polymer hydrolyzed | | |
|---|---|---|---|---|---|
| | | | 100° C./8 hrs % | 37° C./60 days % | 37° C./90 days % |
| Control | 1.36 | None | 100 | 98.4 | 99.3 |
| 2 | 1.47 | 195–200 | 99.4 | 91.5 | 92.0 |
| 9 | 1.67 | 200–203 | 92.8 | 88.7 | 89.7 |
| 10 | 1.56 | 190–195 | 89.2 | 84.4 | 90.3 |
| 11 | 1.48 | 203–207 | 86.9 | 66.3 | — |

*0.1 percent solution at 25° C. in hexafluoroisopropanol

While the preceding examples have been directed to the preparation of specific copolymers of lactide and glycolide, these examples are for purposes of illustration only and are not limiting of the invention. Mixtures of these polymers with up to about 50 percent by weight of other compatible nontoxic and absorbable polymers are likewise included within the present invention.

It is to be understood that inert additives such as coloring materials and plasticizers can be incorporated with the polymers of the present invention. As used herein, the term "inert" means materials that are chemically inert to the polymer, and biologically inert to living tissue, i.e., do not cause any of the adverse effects previously discussed. Any of a variety of plasticizers such as, for instance, glyceryl triacetate, ethyl benzoate, diethyl phthalate, dibutyl phthalate and bis-2-methoxyethyl phthalate can be used if desired. The amount of plasticizer may vary from 1 to about 20 percent or more based on the weight of the polymer. Not only does the plasticizer render the filaments of the present invention even more pliable, it also serves as a processing aid in extrusion and thread preparation.

Many different embodiments of this invention will be apparent to those skilled in the art and may be made without departing from the spirit and scope thereof. It is accordingly understood that this invention is not limited to the specific embodiments thereof except as defined in the appended claims.

What is claimed is:

1. A method for preparing a crystalline copolymer of lactide and glycolide containing from 50 to 75 wt percent glycolide which comprises:
   a. preparing a random copolymer comprising a major portion of an optically active lactide and a minor portion of a monomer selected from the group consisting of glycolide and d,1-lactide, and
   b. admixing with said random copolymer additional monomers comprising from 70 to 90 wt percent glycolide and 10 to 30 wt percent of an optically active lactide, the quantity of glycolide being sufficient to provide from 50 to 75 wt percent glycolide in the polymer-monomer mixture, and
   c. polymerizing said polymer-monomer mixture to obtain said crystalline copolymer of lactide and glycolide, said copolymer having an inherent viscosity determined as a 0.1% solution in hexafluoroisopropanol at 25° C. of at least about 1.20, a melting point of at least about 160° C. and a crystallinity of at least about 15%.

2. The method of claim 1 wherein said random copolymer comprises from 60 to 90 wt percent of optically active lactide and from 10 to 40 wt percent of another monomer selected from the group consisting of glycolide and d,1-lactide.

3. The method of claim 2 wherein the optically active lactide is L(−)-lactide and the other monomer is glycolide.

4. The method of claim 3 wherein the random copolymer comprises from 65 to 75 wt percent of L(−)-lactide and from 25 to 35 mol percent glycolide.

5. The method of claim 2 wherein the optically active lactide is L(−)-lactide and the other monomer is d,1-lactide.

6. The method of claim 5 wherein the random copolymer comprises from 65 to 75 wt percent of L(−)-lactide and from 25 to 35 wt percent d,1-lactide.

7. The method of claim 1 wherein the optically active lactide admixed with the random copolymer according to Step (b) is L(−)-lactide.

8. The method of claim 7 wherein the mixture of L(−)-lactide and glycolide admixed with the random copolymer according to Step (b) comprises from 80 to 90 wt percent glycolide and from 10 to 20 wt percent L(−)-lactide.

9. The method of claim 1 wherein the random copolymer is ground to produce a particulate material prior to admixing with additional monomers according to Step (b).

10. The copolymer product of the process of claim 1.
11. The copolymer product of the process of claim 3.
12. The copolymer product of the process of claim 6.
13. The copolymer product of the process of claim 8.

* * * * *